US006466673B1

(12) United States Patent
Hardy

(10) Patent No.: US 6,466,673 B1
(45) Date of Patent: Oct. 15, 2002

(54) INTRACRANIAL NOISE SUPPRESSION APPARATUS

(75) Inventor: William C. Hardy, Dallas, TX (US)

(73) Assignee: MCI Communications Corporation, Washington, DC (US)

( * ) Notice: Subject to any disclaimer, the term of this patent is extended or adjusted under 35 U.S.C. 154(b) by 0 days.

(21) Appl. No.: 09/075,565

(22) Filed: May 11, 1998

(51) Int. Cl.[7] ......................... A61F 11/06; G10K 11/16; H03B 29/00

(52) U.S. Cl. ..................... 381/71.6; 381/71.2; 381/71.3

(58) Field of Search ........................... 381/71.11, 71.12, 381/72, 71.6, 71.2–71.3; 433/27, 229

(56) References Cited

U.S. PATENT DOCUMENTS 5,133,017 A 7/1992 Cain et al. .................... 381/71
5,206,911 A * 4/1993 Eriksson et al. ......... 381/71.11
5,444,786 A * 8/1995 Raviv ...................... 381/71.11
5,570,426 A * 10/1996 Gardner ........................ 381/72
5,692,056 A 11/1997 Gardner ...................... 381/71.2
5,844,996 A * 12/1998 Enzmann et al. ........ 381/71.11

* cited by examiner

*Primary Examiner*—Xu Mei

(57) ABSTRACT

An apparatus for suppressing an induced intracranial noise or vibrational signal within a patient's head due to a drilling or cutting medical instrument. The apparatus includes a mechanism for sensing the intracranial vibrational signal induced within the patient's head. The apparatus also includes a mechanism for adaptively generating an intracranial vibrational suppression signal from the intracranial vibrational signal as a function of time. In addition, the apparatus provides a mechanism for applying the intracranial vibrational suppression signal to the patient's head for suppressing the induced intracranial noise or vibrational signal.

27 Claims, 3 Drawing Sheets

INTRACRANIAL NOISE SUPPRESSION APPARATUS

FIELD OF THE INVENTION

The present invention relates to noise suppression devices and more particularly pertains to actively suppressing vibrational noise produced by a drilling medical instrument in a head of a patient with an intracranial noise suppression apparatus.

DESCRIPTION OF THE PRIOR ART

In a variety of situations, the effect of environmental noise on people ranges from mere annoyance to severe physiological damage. Consequently, control of noise is very important, especially in the workplace, where its adverse consequences can have a great economic impact. Past efforts at noise control have focused on using sound absorbing materials to mitigate the noise or reducing the amount of exteriorly created noise at its source. However, these conventional noise reduction techniques have minimal effect in reducing stress-inducing vibrational noises on a patient produced by a dentist's drill and associated ultrasonic cleaning tools.

Unfortunately, high frequency sounds from drilling and ultrasonic cleaning propagate very effectively through a patient's skull to reach the ear. Consequently, one of the chief complaints received by dentists from their patients is discomfort from noise caused by drilling-type operations in their mouths. Furthermore, the discomfort caused by a drilling noise has been exacerbated due to further increases in the speed of new drilling devices.

Although some noise reduction can be accomplished by muffling a patient's ears or by using active speaker systems to cancel noise that propagates to the patient's ears, these efforts have been largely unsuccessful in lessening a patient's pain, chiefly because they have a negligible effect in reducing the discomfort due to drilling noise as it arrives at the inner ear from propagation paths through the patient's head. For instance, drilling noise induced particularly in the tooth and the jaw by a drill enters the bone and propagates through the skull and its interior to the temporal bone, and finally to the ear. Many dentists have attempted to mask this drilling noise by providing loud music of the patient's choice through headphones. However, this method has been rather ineffective at masking the more intense, bone-conducted high-frequency noise that is most objectionable. Furthermore, the loud music interferes with communication between the dentist and the patient.

Additional attempts have been made to reduce the discomfort of a patient by suppressing vibrations propagating through the bone structure and intracranial tissue of the head due to a drilling medical instrument by using active vibration cancellation. For example, U.S. Pat. No. 5,570,426 to Gardner discloses a method and apparatus for active cancellation of vibrational noise produced by a medical instrument in the head of a patient. Vibrations from the instrument, as well as vibrations in the bone structure of the head of the patient, are sensed and processed to generate canceling noise waves that are then fed into the inner ear through headphones or the like. An equalizer shapes the magnitude and phase spectrum of the vibrational noise signal picked up from the drill and delivers an equalized inverse signal to the patient. An automatic adaptive controller adjusts the output from the equalizer using control signals consisting of vibrations from the bone structure and the drill.

Furthermore, U.S. Pat. No. 5,692,056 to Gardner discloses another apparatus for suppression of vibrational noise produced by a medical instrument in the head of a patient. This apparatus employs head-worn vibrators to cancel drill induced vibration at the inner ear. Referring to FIG. 1, the system of U.S. Pat. No. 5,692,056 includes an equalizer 10 that is electrically connected to a drill vibration pickup 12, such as a conventional accelerometer or the like vibration sensor, which in turn is mechanically coupled to a drill 14. Equalizer 10, the input of which is connected to drill vibration pickup 12 through interconnection 16, shapes the magnitude and phase spectrum of the vibration signal picked up from the drill 14 and delivers equalized output signals to a right head-worn vibrator 18*a* and a left head-worn vibrator 18*b*, to which it is electrically connected through interconnections 20*a* and 20*b*, respectively. The system also includes an adaptive controller 22 that has an input electrically connected to a drill vibrational pickup 12 through interconnection 16 and inputs electrically connected to the right 24*a* and left 24*b* mastoid pickups through interconnections 26*a* and 26*b*, respectively. The right 24*a* and left 24*b* mastoid pickups are conventional accelerometers or like vibration sensors similar to drill vibrational pickup 12. Adaptive controller 22, the output of which is connected to an input of equalizer 10 through interconnection 28, adaptively adjusts equalizer 10 using the vibration signals from drill vibration pickup 12, and right 24*a* and left 24*b* mastoid pickups. The adaptively equalized vibrations emanating from the right 18*a* and the left 18*b* head-worn vibrators are physically introduced into the patient 30 and cause vibrations in the inner ear. The vibration sensors and the vibrators are configured for coupling to the drill and the patient, using conventional coupling mechanisms.

However, the apparatuses disclosed in the '426 and '056 patents require a physical connection to the dentist's drilling device to achieve an effective cancellation of intracranial noise. As such, a special drill with a proper connection must be provided for use, thereby precluding use of these apparatuses with conventional dental drilling-type equipment that is usually available in a dentist's office. These apparatuses also employ a rather complex equalizing and adaptive controlling mechanism that is dependent upon a relatively remote input signal supplied from the drilling device for use in active cancellation of noise. Furthermore, due to direct coupling with the dentist's drill, portability of these apparatuses is restricted. As a result, these apparatuses cannot be readily moved from one location to another for supporting a multitude of drilling operations, such as in a dental office arrangement supporting a variety of dental chairs in separate rooms or areas.

SUMMARY OF THE INVENTION

The apparatus for suppressing intracranial noise substantially departs from the prior art by providing a portable intracranial noise suppression apparatus for actively suppressing vibrational noise produced by a drilling medical instrument in a head of a patient.

The apparatus of the present invention uses an intracranial or vibrational noise signal that is available directly next to a patient's ear as an input, thereby receiving a better estimate of the noise signal for active suppression than by receiving the input from a more remote location.

The apparatus provides an improved system for eliminating objectionable high-frequency sounds that a patient hears while undergoing dental work. In addition, the apparatus can be used when drilling or cutting of bone in a patient's head or elsewhere could cause objectionable noise in the patient's ears, such as during brain surgery. The system does not have to be physically connected to a dentist's drilling equipment to perform its function.

The apparatus can be readily moved from one location to another for supporting a multitude of bone drilling or cutting operations, such as in a dental office arrangement supporting a variety of dental chairs in separate rooms or areas.

The apparatus includes a mechanism for sensing an intracranial vibrational signal induced within a patient's head. The apparatus provides another mechanism for adaptively generating an intracranial vibrational suppression signal from the intracranial vibrational signal as a function of time. In addition, the apparatus includes yet another mechanism for applying the intracranial vibrational suppression signal to the patient's head for suppressing the induced intracranial vibrational signal.

DESCRIPTION OF THE PREFERRED EMBODIMENT

Figure 1:
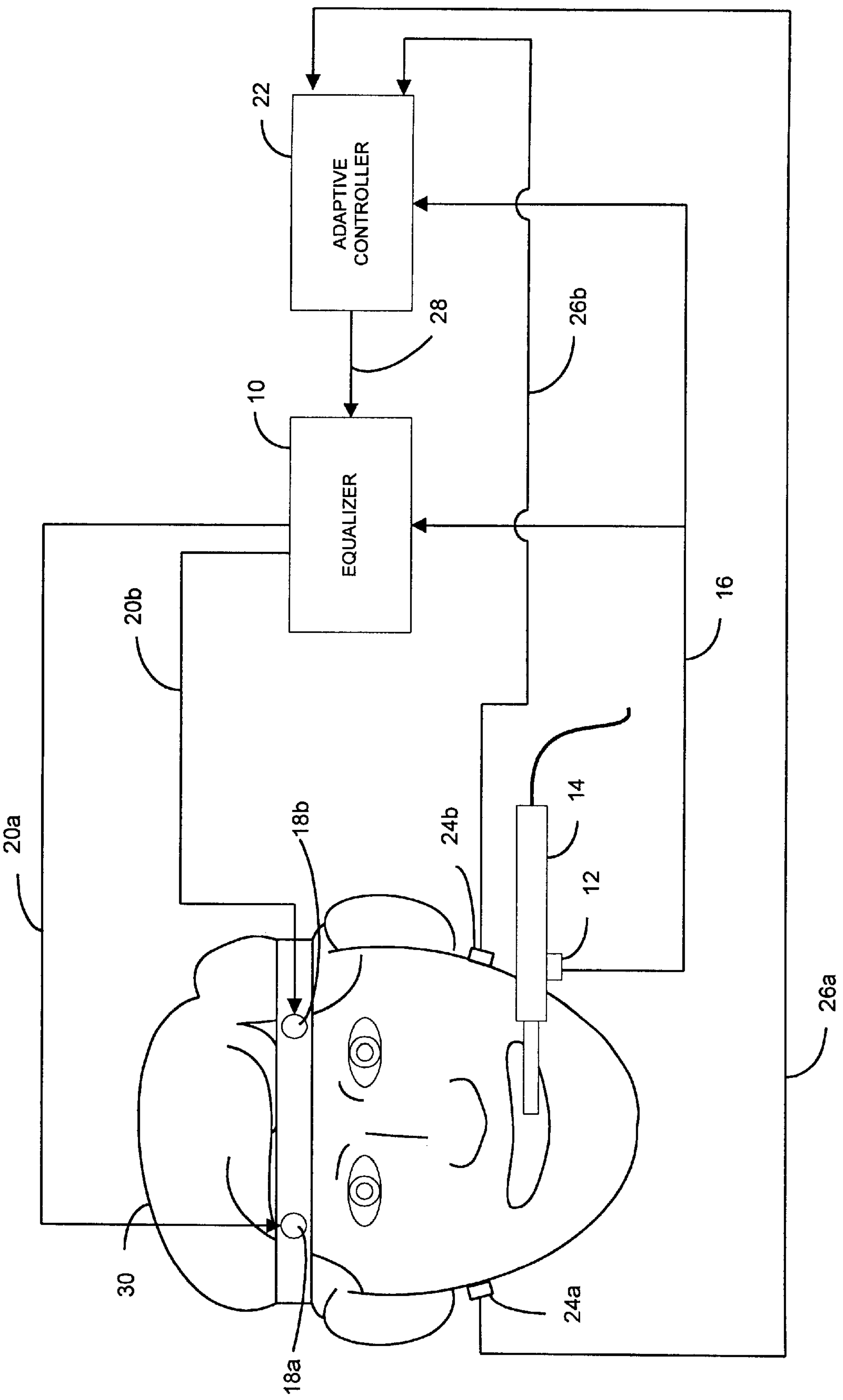
FIG. 1 (PRIOR ART)
FIG. 1 is a prior art apparatus coupled to a patient and a medical instrument for suppressing intracranial noise.
Figure 2:
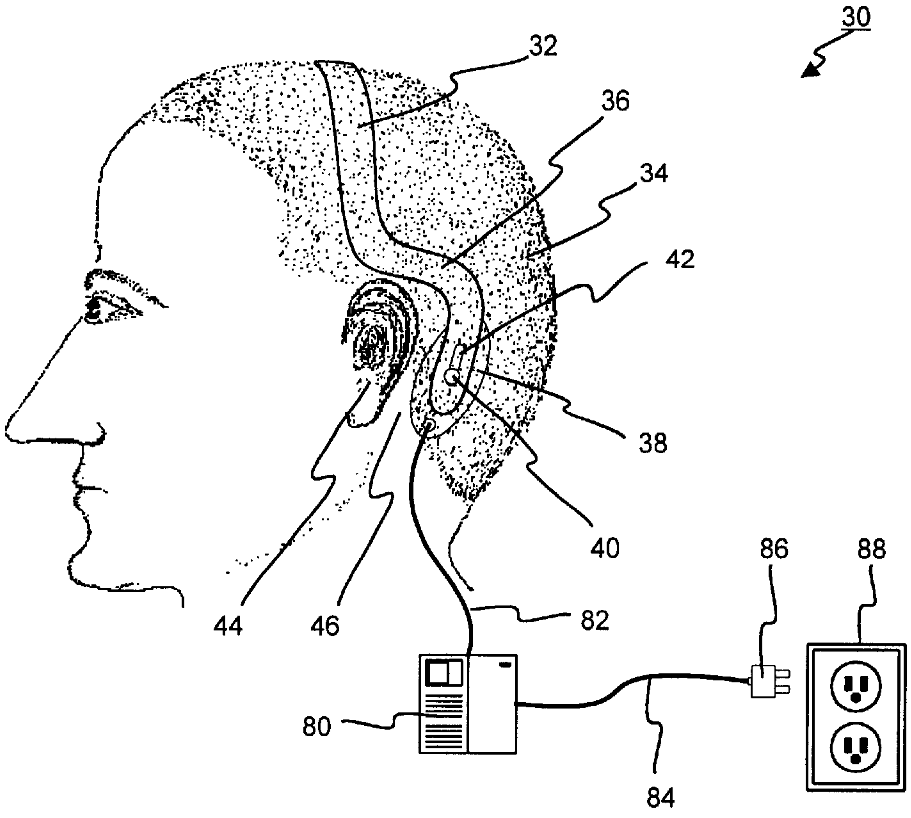
FIG. 2 is a side view of the system of the present invention attached to a patient's head.

The preferred embodiment of the intracranial noise suppression apparatus of the present invention is generally designated by the reference number 30. Referring to FIG. 2, the system 30 of the present invention includes a headset 32. Headset 32 is adapted to be removably secured to a patient's head 34. Headset 32 includes an elongated and adjustable flexible headpiece 36. An adjustable earpiece 38 is secured to each end of headpiece 36 with a pin 40 that is slidably disposed in slot 42. Headpiece 36 is formed with a curvature such that it can be secured to a patient's head and yet not obstruct the patient's ears 44 and impair hearing. As a consequence, since the patient's hearing is not impaired, communication with a dentist can occur in a normal fashion. Each earpiece 38 of headset 32 is readily positionable on a relatively bony part of the patient's head 34, preferably a mastoid 46, which is located on the patient's head 34 directly behind the ear 44.

Figure 3:
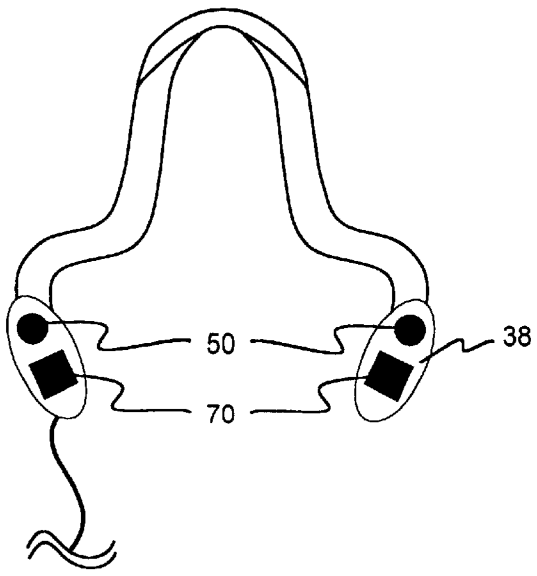
FIG. 3 is a view of the headset of the present invention.
Figure 4:
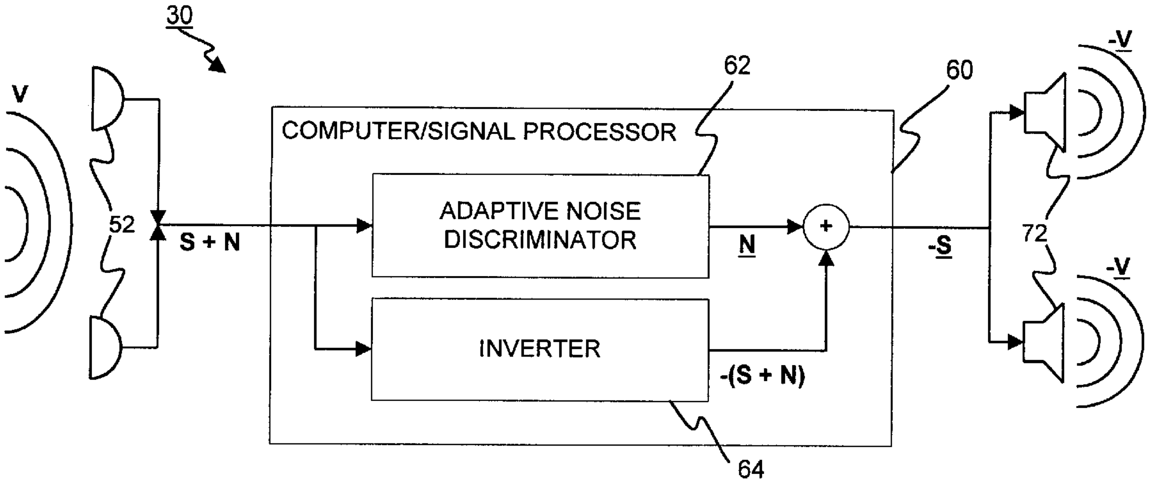
FIG. 4 is a functional block diagram of the present invention depicting the signal flow for suppressing intracranial noise.

Referring to now to FIGS. 3 and 4, each earpiece 38 includes an accelerometer 50 connected thereto for sensing an intracranial vibrational signal V that is induced within a patient's head. The intracranial vibrational signal V can be induced when the patient's tooth or jaw is subjected to dental drilling operations or when the patient's head or remaining skeletal structure is subjected to surgical drilling or cutting operations. Preferably, the accelerometer used is a silicon-fabricated lightweight miniature microphone 52 manufactured by Noise Technologies, Incorporated.

The apparatus 30 also includes a computer or digital signal processor 60. An associated executable adaptive noise discriminator 62 resides on the computer 60. The adaptive noise discriminator, which is implemented in firmware or software, is used for adaptively generating an output intracranial vibrational suppression signal $-\underline{V}$ from the input intracranial vibrational signal V received from the microphone 52 as a function of time, preferably in a near-real time fashion. No other input signal other than signal V is relied upon in generating signal $-\underline{V}$. Signal V is received by the microphone 52 directly at the mastoid 46 of the patient's skull when drilling or cutting operations commence.

In operation, each microphone 52 is coupled to an input of the computer 60 and provides a signal S containing background noise N (S+N) from the time-varying intracranial vibrational signal V. Signal S is the intracranial noise received by the apparatus 30 from the mastoid 46 of the patient's head 34, and signal N is the accompanying extraneous background noise signals from externally-located noise sources. The adaptive noise discriminator determines an estimate of the noise $\underline{N}$ from the input signal S+N. The signal S+N is then inverted with an off-board or on-board inverter 64 and combined with the noise estimate signal $\underline{N}$ to create an inverted signal estimate $-\underline{S}$ of the received intracranial noise signal S. In general, signal $-\underline{S}$ has a polarity opposite that of signal S and a magnitude and a phase substantially similar to signal S. Preferably, the adaptive noise discriminator 62 is comprised of adaptive speech filtering software available from Noise Cancellation Technologies, Incorporated. This adaptive speech filtering software can be executed in near real time on an embedded chip or on a conventional personal computer. A variety of digital signal processors or computers can be used for executing the adaptive speech filtering software, such as the ADSP-2171 digital signal processor or the ADSP-21MSP58 fixed point platform.

Each earpiece 38 also has an output transducer such as a vibrator 70 that is connected thereto and to an output of the computer 60. The vibrator 70 receives signal $-\underline{S}$ as an input and then mechanically produces a time-varying intracranial vibration suppression signal $-\underline{V}$ as an output, which is an inverted estimate of the input signal V. When the headset 32 is secured to the patient's head 34 in the preferred fashion, the output signal $-\underline{V}$ is directed toward and applied to the patient's mastoid 46 for suppressing the induced intracranial vibrational signal V resulting from bone drilling or cutting operations. When the signal $-\underline{V}$ is applied to the bony structure of a patient's head such as the mastoid 46 through use of the vibrator, the signals V and $-\underline{V}$ essentially cancel each other out. As a consequence, high frequency signals are substantially nullified or suppressed, and the patient hears essentially no high pitched noise as a result of drilling or cutting. Preferably, the vibrator used is a miniature lightweight piezoelectric speaker 72 that is relatively flat in shape. This speaker is available from Noise Cancellation Technologies, Incorporated.

Referring again to FIG. 2, the computer 60 is encased in a rigid plastic controller box 80. The microphone 52 and speaker 72 are electrically connected to the computer 60 and controller box 80 through the use of a cable 82. Electrical power is preferably supplied to the apparatus 30 through a power cable 84 that is electrically connected to the controller box 80 and computer 60. The power cable 84 is terminated with a plug 86 for receiving an external source of electrical power through a conventional electrical receptacle 88. Instead of using an external power source, a portable battery or power pack can be used. In either of these configurations, the apparatus 30 is relatively portable and can be readily moved from one location to another in a dentist's office. Furthermore, the apparatus can be used by medical doctors in a variety of surgical applications to suppress objectionable noise in a patient's ears when drilling or cutting bone in the patient's head or elsewhere, such as during brain surgery.

Referring again to FIGS. 3, both the microphone 52 and the speaker 72 on each earpiece 38 are located next to each other to reduce signal interference and distortion when placed on the patient's head 34. At this location, a good estimate of the intracranial vibrational signal V can be obtained for generating the intracranial vibration suppression signal –V̲. Furthermore, at this location the intracranial vibrational signal –V̲ can be directly applied to the source of the drilling or cutting noise to maximize its suppression. However, the position of the speaker 72 and the microphone 52 on the headpiece 36 of the apparatus 30 could also be varied to thereby create a variety of different headset configurations for suppressing bone drilling or cutting noise. For example, the headset 32 could be structured such that the microphone 52 is positionable against the patient's jawbone while the speaker 72 is positionable against the patient's forehead, or vice versa.

Furthermore, although the microphones 52 and the speakers 72 of the apparatus 30 as shown in FIG. 4 are respectively tied to a common input and a common output of the computer 60, other similar noise-suppressing configurations known to those skilled in the art can be used. For example, each microphone-speaker pair on an earpiece 38 could be connected to a separate computer 60, thereby providing a somewhat independent noise suppression capability at each ear 44 of the patient. Another microphone 52 could also be secured to each earpiece 38 and connected to the computer 60 in order to provide a supplemental measurement of the ambient background noise N for use in the discrimination process.

Figure 5:
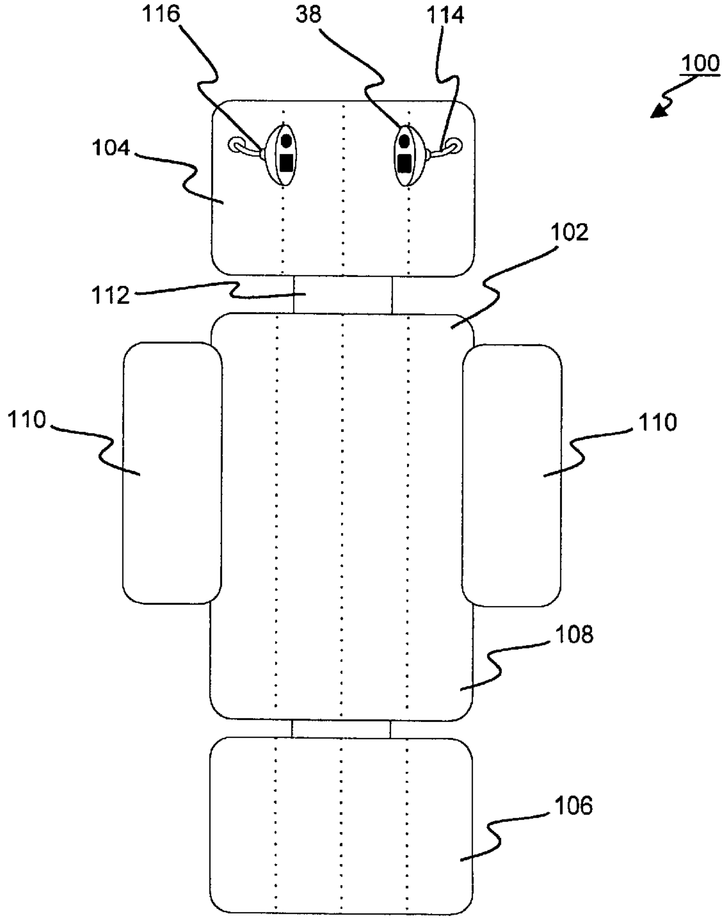
FIG. 5 is a plan view of an alternate embodiment of the system of the present invention secured to a dentist's chair.

A second embodiment of the present invention is shown in FIG. 5. In this embodiment, a dental chair-type apparatus 100 is used for suppressing intracranial noise during dental drilling operations. A dental chair 102 is included. The dental chair is conventional in design and includes a headrest 104, footrest 106, body rest 108, and armrests 110, all supported by a frame 112.

Earpieces 38, which are connected to an unillustrated signal processor or computer as previously set forth, are used for receiving the intracranial vibrational signal V and adaptively generating the intracranial vibration suppression signal –V̲. Each earpiece 38 includes a flexible extendable elongated member 114 that is secured at one end to the headrest 106 and at another end to the earpiece 38 with a ball and socket joint 116. After a patient is positioned in the chair 102, the earpieces 38 are adjusted such that they are in contact with each mastoid 46 of the patient's head 34. Once drilling operations commence, the intracranial vibrational noise signal V can be suppressed as already described.

What is claimed is:

1. An apparatus for suppressing intracranial vibration comprising:

means for sensing an intracranial vibrational signal induced within a patient's head, the intracranial vibrational signal including a vibration signal and a noise signal;

means for adaptively generating an intracranial vibrational suppression signal as a function of time using only the intracranial vibrational signal from the patient's head as an input, the means for adaptively generating including:

means for estimating the noise signal from the intracranial vibrational signal, means for inverting the intracranial vibrational signal, means for combining the estimated noise signal with the inverted intracranial vibrational signal to generate an inverted vibration signal, and means for using the inverted vibration signal as the intracranial vibrational suppression signal; and means for applying the intracranial vibrational suppression signal to the patient's head for suppressing the intracranial vibrational signal.

2. The apparatus for suppressing intracranial noise as set forth in claim 1 and further comprising means for removably securing the means for sensing the intracranial vibrational signal and the means for applying the intracranial vibrational suppression signal to the patient's head.

3. The apparatus as set forth in claim 1 and further comprising means for removably securing the means for sensing the intracranial vibrational signal to a mastoid of the patient's head.

4. The apparatus as set forth in claim 1 and further comprising means for removably securing the means for applying the intracranial vibrational suppression signal to a mastoid of the patient's head.

5. The apparatus as set forth in claim 1 wherein the means for sensing the intracranial vibrational signal comprises an accelerometer.

6. The apparatus as set forth in claim 1 wherein the means for sensing the intracranial vibrational signal comprises a microphone.

7. The apparatus as set forth in claim 1 wherein the means for applying the intracranial vibrational suppression signal comprises a vibrator.

8. The apparatus as set forth in claim 1 wherein the means for applying the intracranial vibrational suppression signal comprises a speaker.

9. The apparatus as set forth in claim 1 wherein the means for applying the intracranial vibrational suppression signal comprises a piezoelectric speaker.

10. The apparatus as set forth in claim 1 wherein the means for applying the intracranial vibrational suppression signal comprises a speaker and wherein the speaker is substantially flat in shape.

11. The apparatus as set forth in claim 1 wherein the means for adaptively generating an intracranial vibrational suppression signal comprises an adaptive noise discriminator.

12. The apparatus as set forth in claim 1 wherein the means for adaptively generating an intracranial vibrational suppression signal comprises a computer.

13. The apparatus as set forth in claim 1 wherein the intracranial vibrational suppression signal has a polarity opposite that of the intracranial vibrational signal.

14. The apparatus as set forth in claim 1 wherein the intracranial vibrational suppression signal has a magnitude substantially equal to that of the intracranial vibrational signal.

15. The apparatus as set forth in claim 1 wherein the intracranial vibrational suppression signal has a phase substantially equal to that of the intracranial vibrational signal.

16. A dental chair-type apparatus for suppressing intracranial vibration, comprising:

a dental chair;

means for sensing an intracranial vibrational signal induced within a patient's head, the intracranial vibrational signal including a vibration signal and a noise signal;

means for adaptively generating an intracranial vibrational suppression signal as a function of time using only the intracranial vibrational signal from the patient's head as an input, the means for adaptively generating including:

means for estimating the noise signal from the intracranial vibrational signal, means for inverting the intracranial vibrational signal, means for combining the estimated noise signal with the inverted intracranial vibrational signal to generate an inverted vibration signal, and means for using the inverted vibration signal as the intracranial vibrational suppression signal;

means for applying the intracranial vibrational suppression signal to the mastoid of the patient's head for suppressing the intracranial vibrational signal;

means for removably securing the means for sensing the intracranial vibrational signal and the means for applying the intracranial vibrational suppression signal to the patient's head; and means for securing both the means for sensing the intracranial vibrational signal and the means for applying the intracranial vibrational suppression signal to the dental chair.

17. The dental chair-type apparatus as set forth in claim 16 wherein the means for sensing the intracranial vibrational signal is positionable against a mastoid of the patient's head.

18. The dental chair-type apparatus as set forth in claim 16 wherein the means for applying the intracranial vibrational suppression signal is positionable against a mastoid of the patient's head.

19. The dental chair-type apparatus as set forth in claim 16 wherein the means for sensing the intracranial vibrational signal comprises an accelerometer.

20. The dental chair-type apparatus as set forth in claim 16 wherein the means for applying the intracranial vibrational suppression signal comprises a vibrator.

21. An apparatus for suppressing intracranial noise induced by a medical instrument, comprising:

means for sensing (i) an intracranial vibration signal from a patient's head and (ii) an associated noise;

means for estimating the associated noise;

means for inverting the intracranial vibration signal;

means for combining the estimated noise with the inverted intracranial vibration signal to generate an intracranial vibrational suppression signal; and means for applying the intracranial vibrational suppression signal to the patient's head.

22. The apparatus of claim 21, wherein said means for estimating the associated noise uses adaptive speech filtering.

23. A system for suppressing an intracranial vibration associated with a patient's head and created by a medical device, comprising: a headset adapted to be removably secured to the patient's head, comprising:

an adjustable headpiece, and a plurality of earpieces coupled to said adjustable headpiece, each of the earpieces comprising:

an accelerometer adapted to sense the intracranial vibration via the patient's head, and an output transducer adapted to suppress the intracranial vibration based on an intracranial vibrational suppression signal; and a signal processor coupled to said accelerometers and said output transducers and adapted to generate the intracranial vibrational suppression signal based on information received from said accelerometers without receiving information directly via the medical device, the signal processor comprising:

an adaptive noise discriminator configured to estimate a noise signal from an intracranial vibration signal that is based on the intracranial vibration sensed by the accelerometers, an inverter configured to invert the intracranial vibration signal, and summation logic configured to combine the estimated noise signal with the inverted intracranial vibration signal to generate the intracranial vibrational suppression signal.

24. An apparatus for suppressing intracranial vibration, comprising:

means for sensing an intracranial vibrational signal induced within a patient's head, the intracranial vibrational signal including a vibration signal and a noise signal;

means for estimating the noise signal from the intracranial vibrational signal;

means for inverting the intracranial vibrational signal;

means for combining the estimated noise signal with the inverted intracranial vibrational signal to generate an inverted vibration signal; and means for applying the inverted vibration signal to the patient's head for suppressing the vibration signal.

25. A dental chair-type apparatus for suppressing intracranial vibration, comprising:

a dental chair;

means for sensing an intracranial vibrational signal induced within a patient's head, the intracranial vibrational signal including a vibration signal and a noise signal;

means for estimating the noise signal from the intracranial vibrational signal;

means for inverting the intracranial vibrational signal;

means for combining the estimated noise signal with the inverted intracranial vibrational signal to generate an inverted vibration signal;

means for applying the inverted vibration signal to the mastoid of the patient's head for suppressing the vibration signal; and means for securing both the means for sensing the intracranial vibrational signal and the means for applying the intracranial vibrational suppression signal to the dental chair.

26. A system for suppressing an intracranial vibration associated with a patient's head and created by a medical device, comprising:

an accelerometer adapted to sense the intracranial vibration via the patient's head;

an adaptive noise discriminator configured to estimate a noise signal from an intracranial vibration signal that is based on the intracranial vibration sensed by the accelerometers;

an inverter configured to invert the intracranial vibration signal;

summation logic configured to combine the estimated noise signal with the inverted intracranial vibration signal to generate an intracranial vibrational suppression signal; and an output transducer adapted to suppress the intracranial vibration based on the intracranial vibrational suppression signal.

27. A system for suppressing intracranial vibrations caused by a medical device, comprising:

a head set configured to be removably secured to the head of a patient, the head set comprising:

one or more accelerometers configured to capture an intracranial vibration signal from the head of the patient, the intracranial vibration signal including a vibration signal and a noise signal, and one or more transducers configured to transmit a vibration suppression signal to the head of the patient to suppress the intracranial vibrations caused by the medical device; and a signal processor coupled to the one or more accelerometers and the one or more transducers, the signal processor comprising:

an adaptive noise discriminator configured to estimate the noise signal from the intracranial vibration signal from the one or more accelerometers, an inverter configured to invert the intracranial vibration signal, and summation logic configured to combine the estimated noise signal with the inverted intracranial vibration signal to generate the vibration suppression signal.

* * * * *